US005718665A

United States Patent [19]

Stubbs

[11] Patent Number: 5,718,665

[45] Date of Patent: Feb. 17, 1998

[54] ANIMAL SPECULUM AND METHOD OF USE

[76] Inventor: R. Clay Stubbs, Rt. 2, Box 18, Spicewood, Tex. 78669

[21] Appl. No.: 844,201

[22] Filed: Apr. 18, 1997

[51] Int. Cl.[6] ....... A61B 17/00

[52] U.S. Cl. ....... 600/243; 600/237

[58] Field of Search ....... 600/214, 219, 600/222, 220, 225, 235, 237, 238, 243, 244; 119/821, 831, 833; 433/1, 140; 54/8, 9

[56] References Cited

U.S. PATENT DOCUMENTS 976,812 11/1910 Koehler ....... 600/244

FOREIGN PATENT DOCUMENTS 322561 2/1903 France ....... 600/243

15458 of 1901 United Kingdom ....... 600/243

18199 of 1902 United Kingdom ....... 600/243

441937 1/1936 United Kingdom ....... 600/244

OTHER PUBLICATIONS

Vorhes, Gary; "Straight Into the Horse's Mouth"; Western Horseman (Magazine); pp. 18–23, Oct. 1996.

*Primary Examiner*—Jeffrey A. Smith
*Attorney, Agent, or Firm*—Ted Masters

[57] ABSTRACT

A speculum (20) for opening the jaws of animals (500) includes first (22) and second (30) arms connected by a threaded rod (38). By rotating threaded rod (38), the distance (D) between first (22) and second (30) arms may be selective adjusted. First (22) and second (30) arms have first (28) and second (36) jaw plates respectively, which forcibly open the jaws (502) and (506) of the animal (500). A tension-producing means (100) holds speculum (20) in place in the animal's (500) mouth.

13 Claims, 6 Drawing Sheets

ANIMAL SPECULUM AND METHOD OF USE

TECHNICAL FIELD

The present invention pertains to devices for forcibly opening the jaws of animals, and holding the jaws in an open position for veterinary purposes.

BACKGROUND ART

Specula and the like for forcibly opening the jaws and mouths of animals are well known in the art. These devices are typically positioned between the upper and lower jaws of the animal, and various means are provided to urge the jaws apart. In so doing, access to the mouth and teeth is obtained for the purposes of examination and medical procedures. For example, U.S. Pat. No. 404,652 shows a veterinary mouth speculum for a horse or other animal. The devices holds the jaws of the animal in an open position for veterinary purposes. Two jaw pieces are pivotally connected to the ends of two arms. The two arms are connected to opposite ends of a handle which can be selectively rotated to increase or decrease the distance between the jaw pieces. U.S. Pat. No. 585,101 defines a veterinary mouth speculum having a supporting bow or yoke of essentially semicircular shape. The two ends of the bow are connected to upper and lower jaws respectively by ratchet mechanisms. The upper and lower jaws of the speculum are placed around the upper and lower jaws of the animal, and the ratchet mechanisms are utilized to retain the animal's jaws in the desired open position. U.S. Pat. No. 2,516,413 depicts an apparatus for treating meteorism or tympanites in animals, particularly horned cattle. The apparatus includes two members forming first class levers which are joined in a scissor-like manner. A spring urges the levers into an open position, thereby forcing the animal to open its mouth. U.S. Pat. No. 2,581,679 discloses a device for the relief of bloat in cattle. The device includes a bit-like metal or plastic frame, which is secured in place in the animal's mouth and remains in position until the condition of bloat is fully relieved. U.S. Pat. No. 2,587,245 comprises a combined mouth speculum and tongue support. A main mouth prop or post is bifurcated longitudinally so as to receive a rod which carries a tongue support. The rod is mounted on a slidable sleeve which is adjustable in any conceivable position lengthwise of the prop. U.S. Pat. No. 2,844,142 consists of a device for constraining the tongue. The device comprises a pair of loops, of different size, the smaller of the loops being pendently supported within the larger loop and being, comprised of an elastic substance. U.S. Pat. No. 3,734,084 describes a mechanical tongue depressor having a laterally offset clamp which enables it to be readily clamped to any portion of the vertical post of a conventional mouth speculum wherein the vertical post extends between the upper and lower jaws of the mouth alongside the mouth cavity. U.S. Pat. No. 4,450,831 includes a self supporting mouth speculum for horses, mules, and other animals. The speculum has first and second cheek hooks adjustably connected together by a pair of straps extending therebetween.

In contrast to the aforementioned devices, the present invention offers a much improved full-mouth speculum, as is described in the October 1996 issue of "Western Horseman"

DISCLOSURE OF INVENTION

The present invention is directed to a speculum for forcibly opening the mouth and jaws of an animal for examination, dentistry, or other medical procedures. The present invention comprises a simple, light weight, low maintenance device with a large mechanical advantage so that any size animal's mouth can be easily opened against its will. The speculum is self-retaining, and therefore much safer for the veterinarian to use than other devices which can on occasion permit the animal to bite the hand or finger of the user. The principles of the present invention can be practiced on virtually any animal, but the invention is especially suited to horses and other members of the equine species. Historically equine mouth speculums are operated by hinges positioned lateral to the horse's cheek teeth so that when the mouth is opened, ratchets on each side hold the instrument open. If the animal does not open its mouth voluntarily, then the jaws would have to be spread apart by hand. The present invention by contrast can force the mouth open by turning a threaded rod which causes jaw (tooth) plates to move apart and therefore force the mouth open to any desired degree, and retain the mouth in the open position. The threaded rod and the attached pivoting arms can then be swiveled to either side of the horses jaws (face) to move them out of the way to obtain access to the different parts of the animal's mouth. The jaw plates are preferably held against the horses incisor (front) teeth by an adjustable harness having an elastic band which is placed around the poll of the horse (back of the head). Small strings or cords attach the speculum to the elastic band to provide a minimum of obstruction while working in the mouth. The present invention can be opened or closed with a simple ratchet handle (mechanic's tool) or an electric drill. If an emergency arises, the speculum can be rapidly removed by simply pulling it forward and out of the animal's mouth. Nothing needs to be unbuckled as is the case with a leather harness.

In accordance with a preferred embodiment of the invention, a speculum for the jaws of an animal comprises a first arm having a first end and an opposite second end, a first jaw (tooth) plate is pivotally connected to the first end of the first arm. A second arm is oriented substantially parallel to the first arm, the second arm having a first end and an opposite second end. A second jaw plate is pivotally connected to the first end of the second arm. A threaded rod is oriented substantially perpendicular to and has an end portion rotatably connected to the first arm. The threaded rod has a second end opposite to the end portion. The threaded rod is received by a threaded aperture in the second arm, so that the first arm and the second arm are separated by a distance, and that by rotating the threaded rod, the distance between the first and second arms may be selectively adjusted. A retaining means keeps the first and second arms rotationally aligned around the threaded rod.

In accordance with an important feature of the invention, the second end of the threaded rod includes a socket, so that the threaded rod may be rotated by a ratchet or powered rotational tool such as an electric drill.

In accordance with an important aspect of the invention, once inserted between the jaws of the animal, the first and second arms may be selectively pivoted to either the right or left side of the animals jaws (face) to better obtain access to the inside of the mouth.

In accordance with another important feature of the invention, the first jaw plate is contoured to receive the lower front teeth (incisors) of the animal, and the second jaw plate is similarly contoured to receive the upper front teeth.

In accordance with a preferred embodiment of the invention, the first and second jaw plates are connected to the back portion of the horses's head (poll) by a tension-producing means, so that the speculum exerts a force on the upper and lower front teeth which is directed toward the back portion, and the speculum is thereby retained in place in the animal's mouth.

Other features and advantages of the present invention will become apparent from the following detailed description, taken in conjunction with the accompanying drawings, which illustrate, by way of example, the principles of the invention.

MODES FOR CARRYING OUT THE INVENTION

Figure 1:
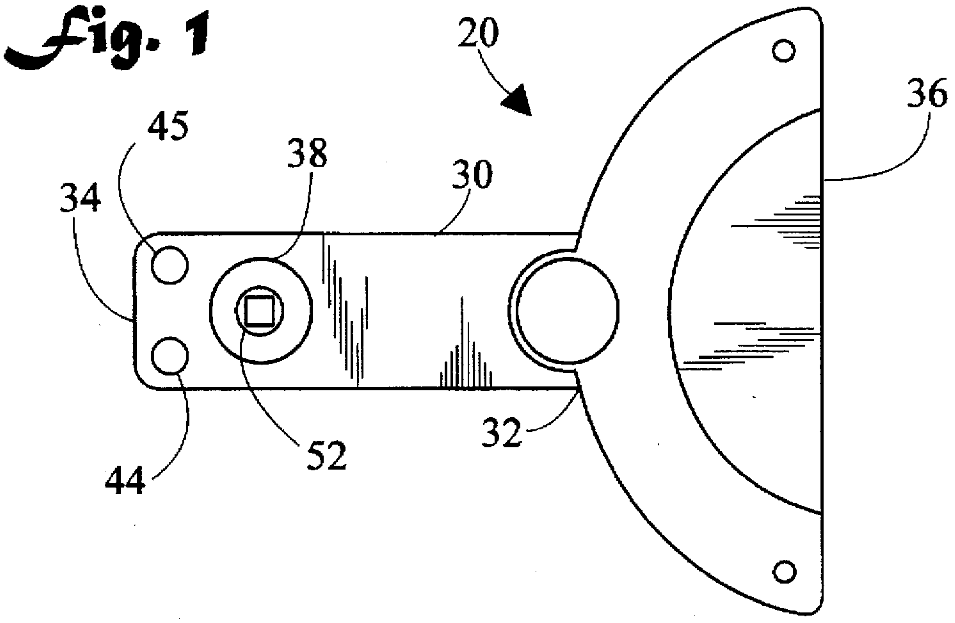
FIG. 1 is a top plan view of a speculum, in accordance with the present invention.
Figure 2:
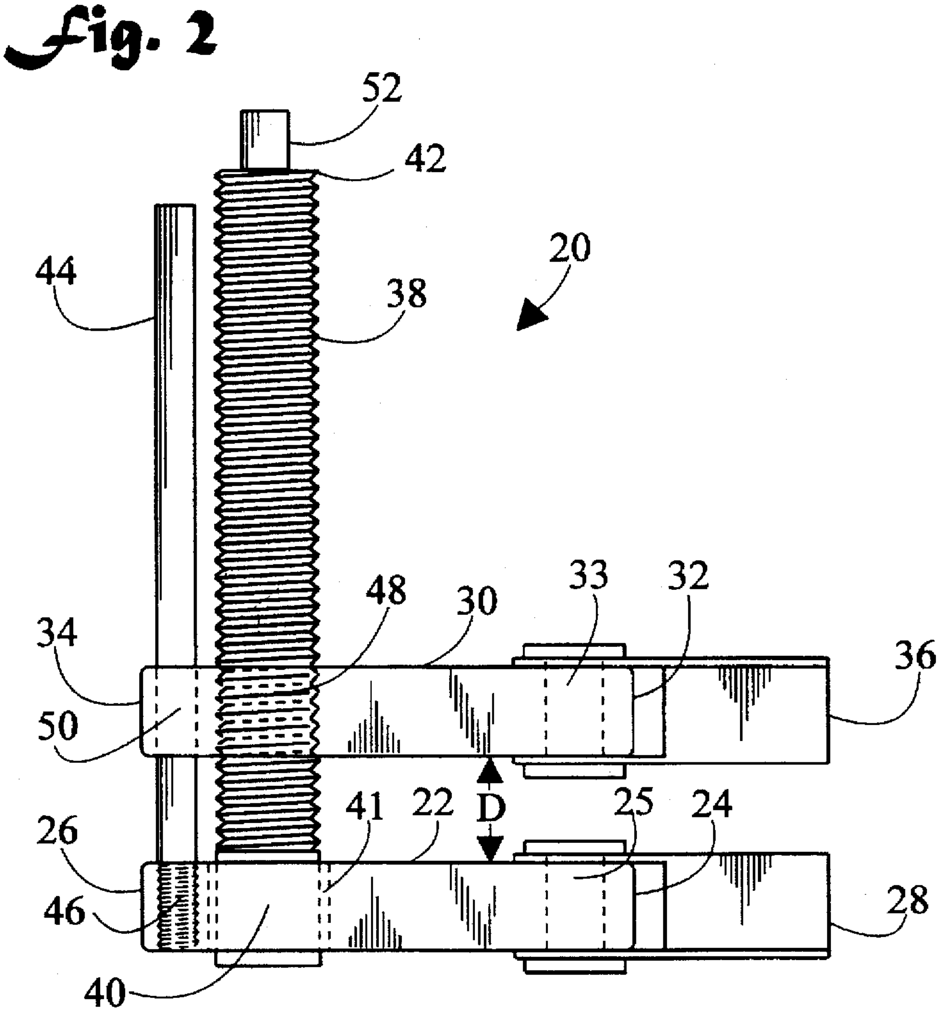
FIG. 2 is a side elevation view of the speculum.
Figure 3:
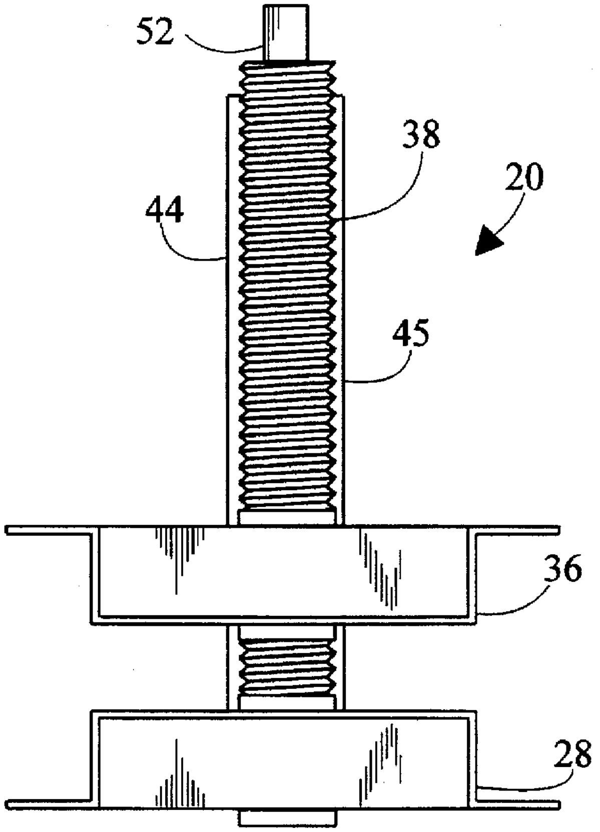
FIG. 3 is a front elevation view of the speculum.
Figure 4:
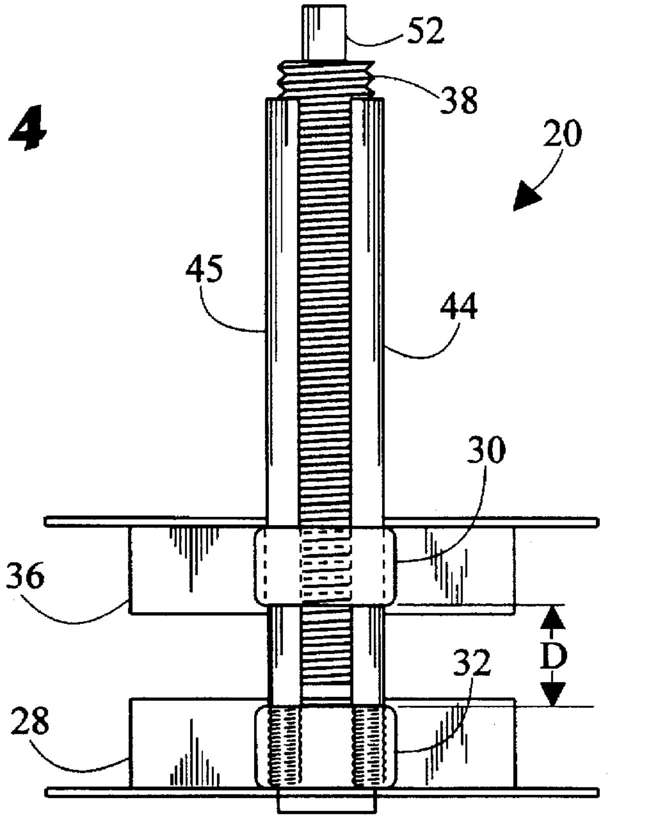
FIG. 4 is a rear elevation view of the speculum.

Referring initially to FIGS. 1 through 4, there are illustrated top plan, side elevation, front elevation, and rear elevation views respectively of a speculum for the jaws of an animal in accordance with the present invention, generally designated as 20. Speculum 20 includes a first arm 22 having a first end 24 and an opposite second end 26. A first jaw plate 28 is pivotally connected to first end 24 of first arm 22 by means of first pin 25. A second arm 30 is oriented substantially parallel to first arm 22. Second arm 30 has a first end 32 and an opposite second end 34. A second jaw plate 36 is pivotally connected to first end 32 of second arm 30 by means of second pin 33. The animal 500 (refer to FIG. 8) has a lower jaw 502 having lower front (incisor) teeth 504 (hidden), and an upper jaw 506 having upper front teeth 508 (hidden). First jaw plate 28 is contoured to receive the lower front teeth 504, and second jaw plate 36 is contoured to receive the upper front teeth 508 (refer also to FIG. 7). Jaw plates 28 and 36 are oppositely oriented to accommodate the animal's 500 upwardly and downwardly projecting teeth respectively. It may be readily appreciated that speculum 20 could be inverted so that first jaw plate 28 is contoured to receive the upper front teeth 508, and second jaw plate 36 is contoured to receive the lower front teeth 504.

A threaded rod 38 has a first unthreaded end 40 rotatably connected to first arm 22 by means of bushing 41, and a second end 42 opposite to unthreaded end 40. Threaded rod 38 is oriented substantially perpendicular to first arm 22. Second arm 30 has a threaded aperture 48 which threadably receives threaded rod 38. A retaining means keeps first arm 22 and second arm 30 rotationally aligned around threaded rod 38. In the shown embodiment the retaining means includes at least one guide rod 44 having an end 46 fixedly connected to first arm 22. Guide rod 44 is oriented substantially perpendicular to first arm 22, and therefore substantially parallel to threaded rod 38. Second arm 30 also has at least one aperture 50 which slidably receives at least one guide rod 44. In the shown embodiment two guide rods, 44 and 45, are provided. The retaining means, for example guide rods 44 and 45, is extremely important in that it maintains first arm 22 and second arm 30 in a ridged aligned rotational relationship with respect to threaded rod 38. Absent guide rods 44 and 45, first arm 22 and second arm 30 could independently pivot around threaded rod 38, making it easier for the animal 500 (refer to FIG. 8) to dislodge speculum 20 by laterally moving its lower jaw 502. It may be readily appreciated that other retaining means could also be employed. For example, extending members could be attached to the sides of first arm 22 that would retain second arm 30 in a captured and therefore mutually aligned configuration. Second arm 30 is located a distance D from first arm 22. By rotating threaded rod 38, second arm 30 moves along threaded rod 38, and thereby the distance D between first arm 22 and second arm 30 may be selectively adjusted (refer also to FIG. 6). A socket 52 is connected to second end 42 of threaded rod 38. Socket 52 is adapted to receive a manual or powered rotational tool to rotate threaded rod 38.

Figure 5:
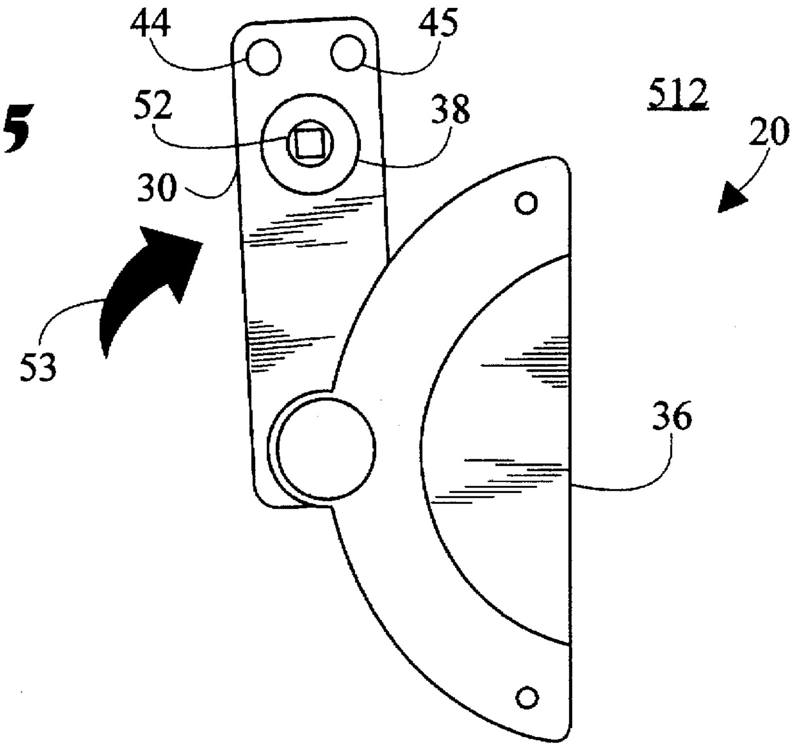
FIG. 5 is top plan view of the speculum, showing the arms pivoted to one side.

FIG. 5 is top plan view of the speculum, show first arm 22 (hidden) and second arm 30 pivoted to one side of the animal's 500 jaws (face) so that arms 22 and 30 of speculum 20 are out of the way, thereby permitting greater veterinary access. Also referring to FIG. 8, the jaws of animal 500 include a right side 512 (hidden) and a left side 510. First and second arms 22 and 30, are selectively pivotable to either the right side 512 or the left side 510. As shown in FIG. 5, arms 22 and 30 have been pivoted in direction 53 to the right side 512.

Figure 6:
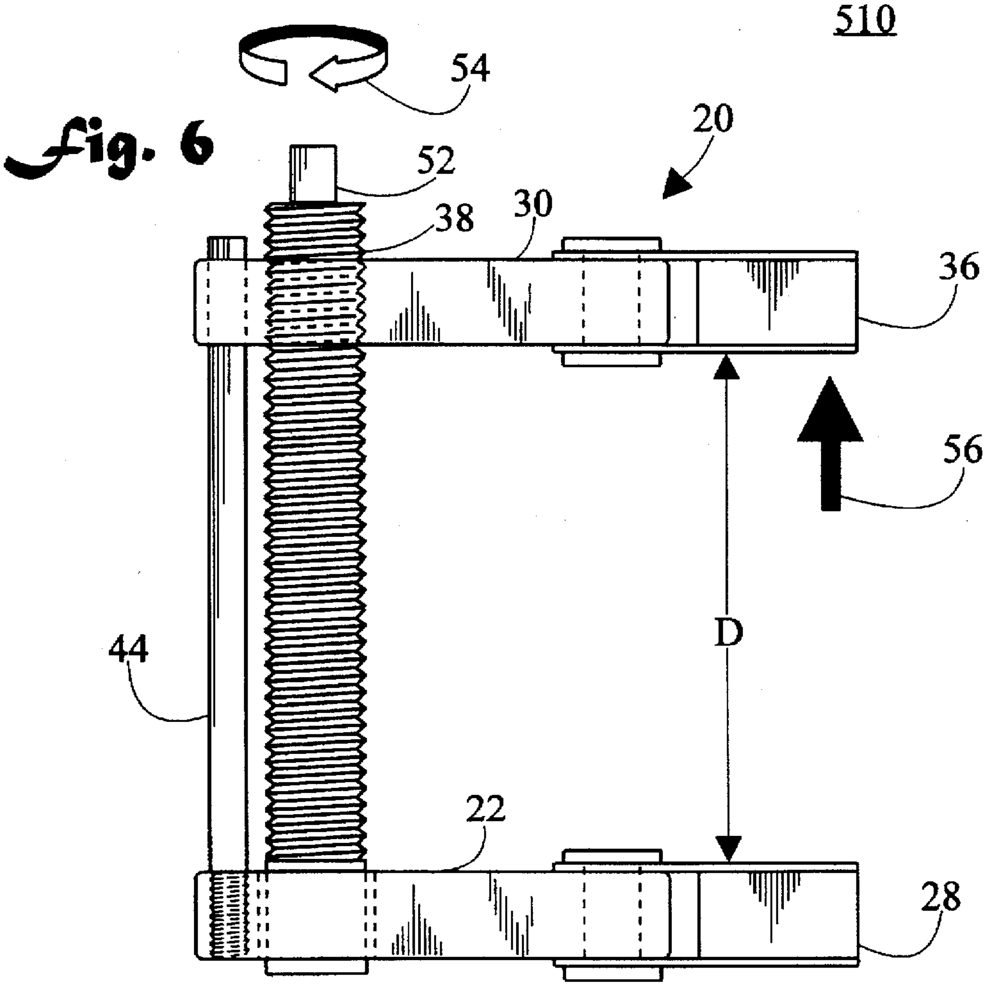
FIG. 6 is a side elevation view of the speculum, showing the second arm moved away from the first arm by the rotation of a threaded rod.

FIG. 6 is a side elevation view of speculum 20, showing second arm 30 moved away from first arm 22 by the rotation of a threaded rod 38. As threaded rod 38 is rotated in clockwise direction 54, second arm 30 moves up threaded rod 38 in direction 56, thereby increasing the distance D between first arm 22 and second arm 30.

Figure 7:
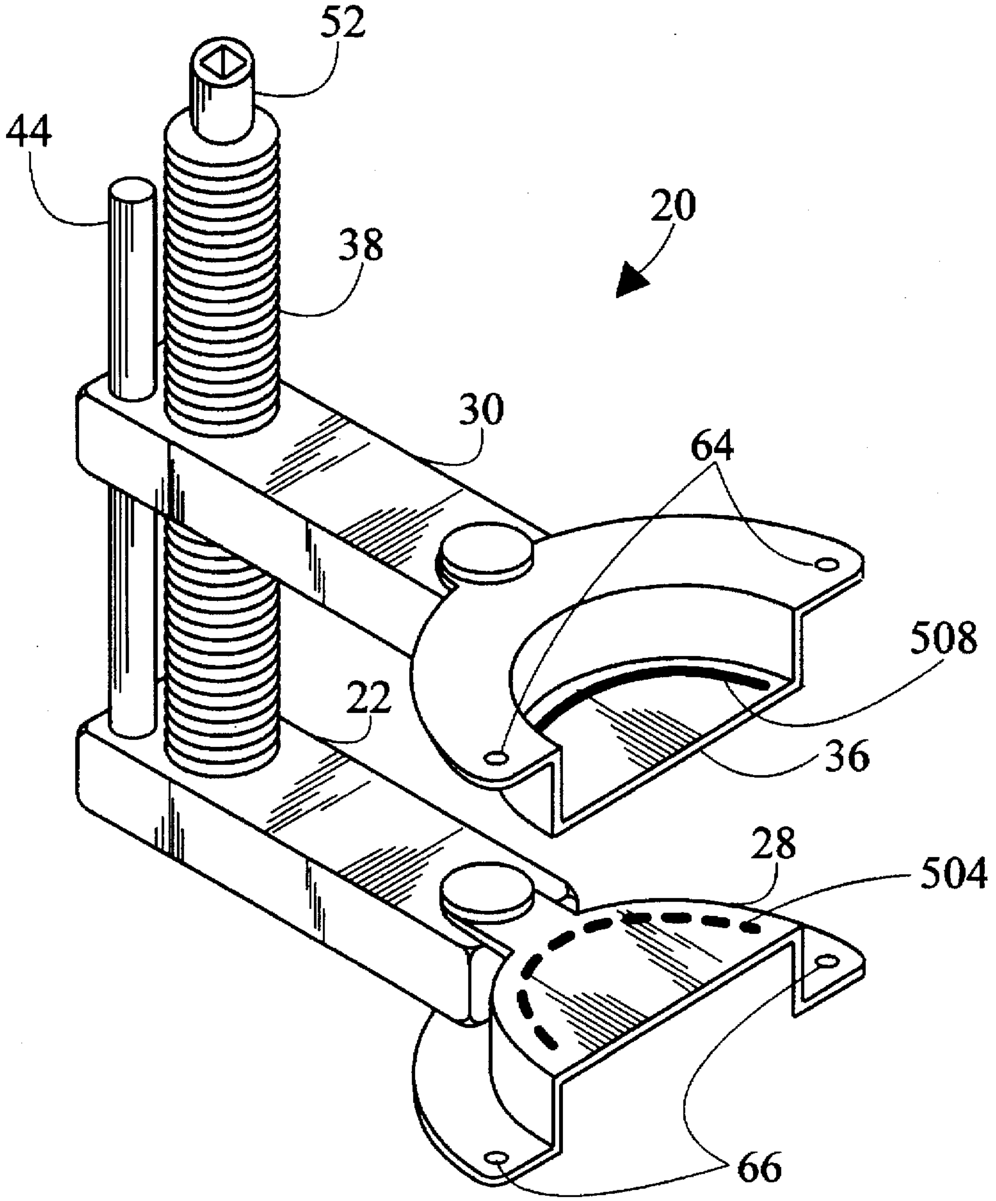
FIG. 7 is a perspective view of the speculum.

FIG. 7 is a perspective view of speculum 20 showing the placement of upper front teeth 508 and lower front teeth 504 in second jaw plate 36 and first jaw plate 28 respectively.

Figure 8:
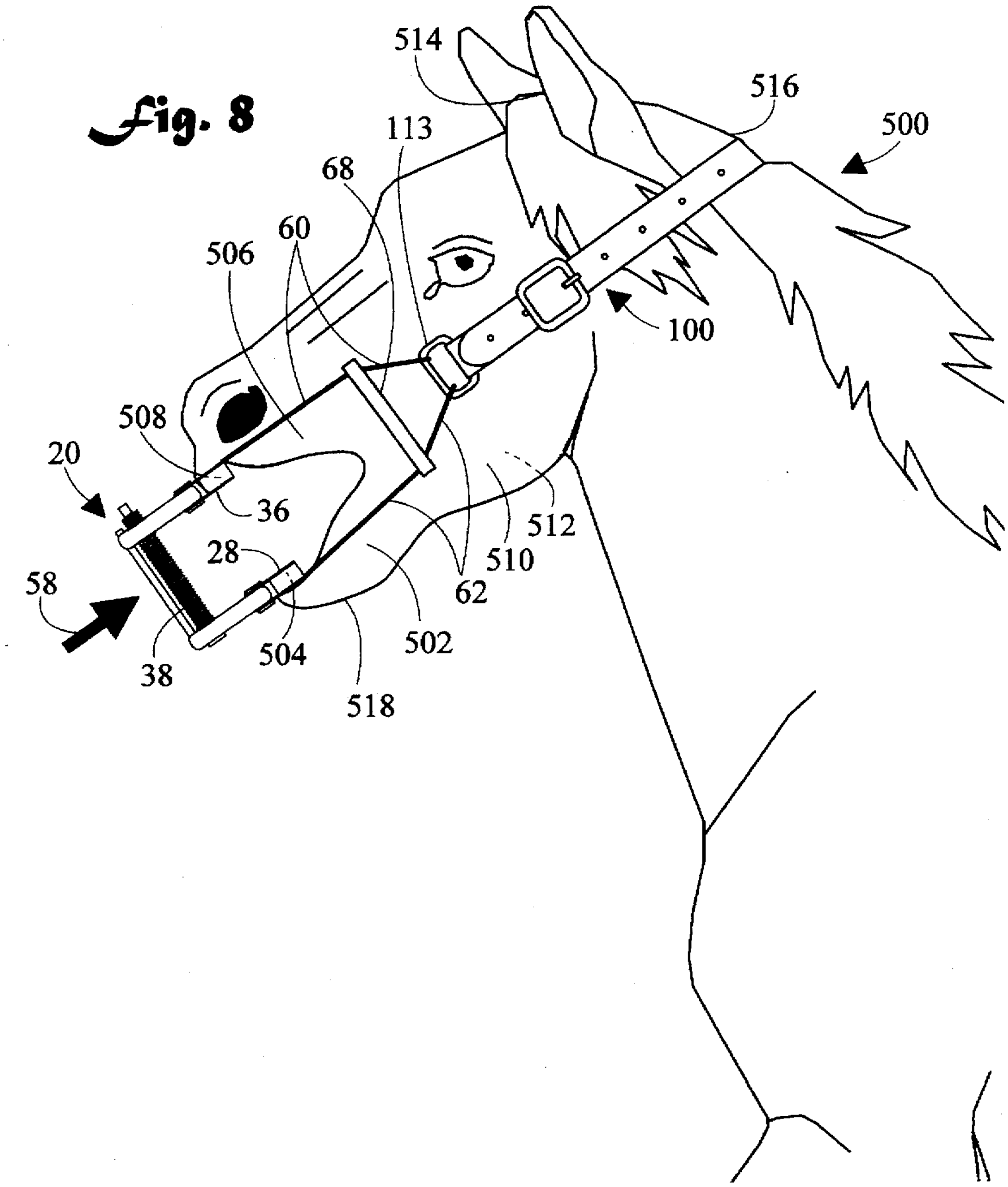
FIG. 8 is a reduced side elevation view of the speculum installed between the jaws of a horse; and, FIG. 9 is a perspective view of a tension-producing means.

FIG. 8 is a reduced side elevation view of speculum 20 installed between the jaws of an animal. First jaw plate 28 receives lower front teeth 504, and second jaw plate 36 receives upper front teeth 508. Threaded rod 38 has been rotated so that lower jaw 502 and upper jaw 506 have been forced apart. The animal 500 further has a head 514 having a back portion or poll 516. First and second jaw plates 28 and 36 are connected to back portion 516 by a tension-producing means 100, so that speculum 20 exerts a force on the upper and lower teeth 508 and 504. The force is directed toward back portion 516 in direction 58. That is, speculum 20 is urged into the animal's 500 mouth by tension-producing means 100. This is highly advantageous in that should speculum 20 somehow become dislodged from upper and lower front teeth 508 and 504, speculum 20 will be pulled deeper into the animal's 500 mouth, thereby preventing the animal 500 from closing its jaws and biting the veterinarian. Tension-producing means 100 is connected to speculum 20 by strings or cords 60 and 62 which connect, by tieing, to upper jaw plate 36 and lower jaw plate 28 respectively. Holes 64 and 66 in upper jaw plate 36 and lower jaw plate 28 accommodate the cord connection (refer to FIG. 7). Left and right spacers 68 route the cords above and below the animal's 500 open mouth so as not to interfere with the veterinary procedures.

Figure 9:
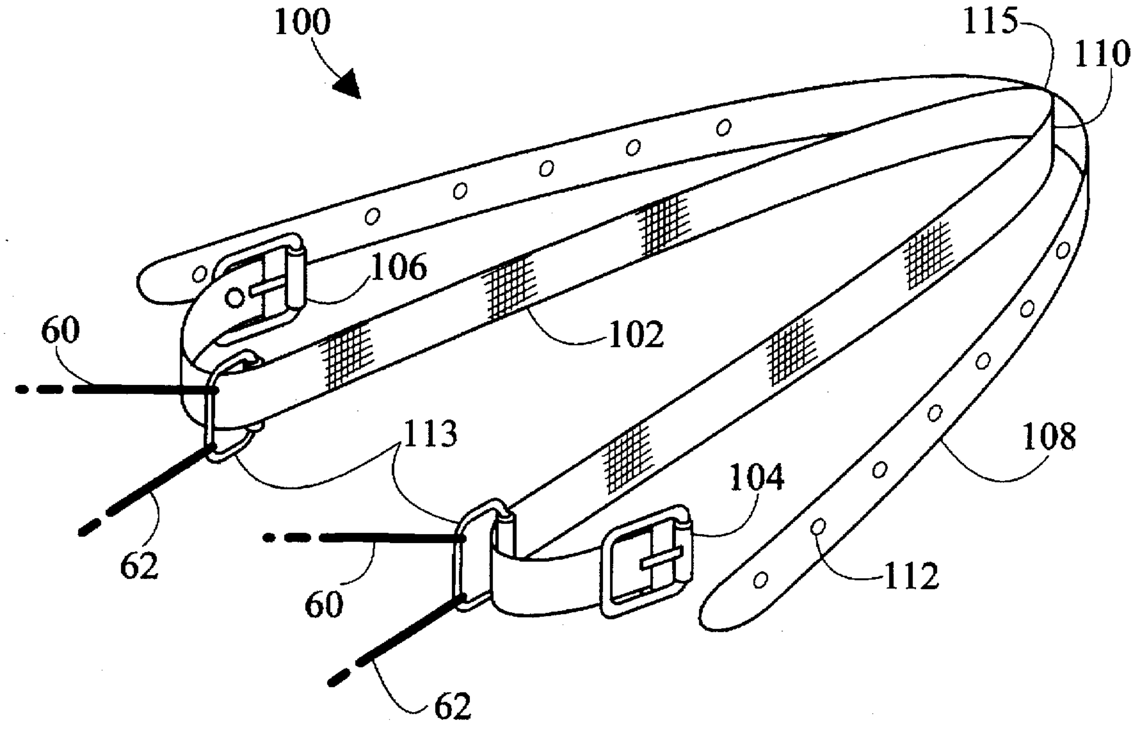

FIG. 9 is a perspective view of a preferred embodiment of tension-producing means 100, comprising a harness having an elastic band 102, and having a first end 113 comprising a pair of buckles and an opposite second end 115. Elastic band 102 has left and right buckles 104 and 106, and is sewed to a nylon belt 108 along seam 110 at second end 115. Holes 112 permit nylon belt 108 to be adjust in length to accommodate the size of the animal 500. In a preferred embodiment, first end buckles 113 and 115, as well as left and right buckles 104 and 106 are roller buckles. It may be readily appreciated that numerous other tension-producing means 100 arrangements could also be employed.

Speculum 20 can be used to spread the jaws of an animal 500 as follows (refer to FIGS. 8 and 9 ): Threaded rod 38 is rotated until first arm 22 and second arm 36 are separated by a predetermined distance D. Predetermined distance D is relatively small so that jaw plates 28 and 36 may conveniently placed in the partially open mouth of animal 500. A tension-producing means 100 is provided, the tension-producing means 100 has a length, a first end 113, and a second end 115. First end 113 is connected to jaw plates 28 and 36 of speculum 20. In the shown embodiment, the connection is effected with cords 62 and 60 respectively, and spreader 68. Second end 115 of tension-producing means 100 is placed around back portion 516 of the animal's head 514. The length of tension-producing means 100 is then adjusted using nylon belt 108 and buckles 104 and 106, so that speculum resides slightly behind and below the chin 518 of the animal. Belt 108 tightness is adjustable from both sides. Tension-producing means 100 is then stretched, and speculum 20 is inserted between the animal's 500 jaws, so that first jaw plate 28 receives the lower front teeth 504 and second jaw plate 36 receives the upper front teeth 508. Threaded rod 38 is then rotated so that the predetermined distance is increased thereby urging jaws 502 and 506 apart.

In a preferred embodiment, threaded rod 38 has a socket 52 connected to second end 42. A powered rotational tool (such as a drill motor) is inserted into socket 52, and the powered rotational tool is used to effect the rotation of threaded rod 38. After the jaws have been opened the desired distance, first and second arms 22 and 30 are selectively pivoted out of the way either to the right or left side of the animal's jaws.

Because of the elasticity of tension-producing means 100, Speculum 20 can be disengaged by simply pulling it forward to remove it from the animal's 500 teeth and jaws.

Speculum 20 may be fabricated from a variety of materials. Steel or stainless steel with a brass bushing have been found useful. In a preferred embodiment, belt 108 of tension-producing means 100 is fabricated from nylon which can be easily cleaned and sterilized. Elastic band 102 can be fabricated from a variety of commercially available products.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A speculum for the jaws of an animal, comprising:

a first arm having a first end and an opposite second end, a first jaw plate pivotally connected to said first end of said first arm;

a second arm oriented substantially parallel to said first arm, said second arm having a first end and an opposite second end, a second jaw plate pivotally connected to said first end of said second arm;

a threaded rod, said threaded rod having an end portion rotatably connected to said first arm, said threaded rod substantially perpendicular to said first arm, said threaded rod having a second end opposite to said end portion;

said second arm having a threaded aperture which threadably receives said threaded rod, said second arm located a distance from said first arm;

so that by rotating said threaded rod, said distance may be selectively adjusted;

at least one guide rod, said at least one guide rod having an end connected to said first arm, said at least one guide rod substantially perpendicular to said first arm; and, said second arm having at least one aperture which slidably receives said at least one guide rod.

2. A speculum according to claim 1, further including a socket connected to said second end of said threaded rod.

3. A speculum according to claim 1, the jaws of the animal having a right and left side, said first and second arms selectively pivotable to either the right or left side.

4. A speculum according to claim 1, the animal having a lower jaw having lower front teeth, and an upper jaw having upper front teeth, said first jaw plate contoured to receive the lower front teeth, and said second jaw plate contoured to receive the upper front teeth.

5. A speculum according to claim 4, the animal having a head having a back portion, further including:

said first jaw plate receiving the lower front teeth, and said second jaw plate receiving the upper front teeth; and, said first and second jaw plates connected to the back portion by a tension-producing means, so that said speculum exerts a force on the upper and lower front teeth, said force directed toward the back portion.

6. A speculum according to claim 5, wherein said tension producing means comprises a harness having an elastic band.

7. A speculum according to claim 1, the animal having a lower jaw having lower front teeth, and an upper jaw having upper front teeth, said first jaw plate contoured to receive the upper front teeth, and said second jaw plate contoured to receive the lower front teeth.

8. A speculum according to claim 7, the animal having a head having a back portion, further including:

said first jaw plate receiving the upper front teeth, and said second jaw plate receiving the lower front teeth; and, said first and second jaw plates connected to the back portion by a tension-producing means, so that said speculum exerts a force on the upper and lower front teeth, said force directed toward the back portion.

9. A speculum according to claim 8, wherein said tension producing means comprises a harness having an elastic band.

10. A method for spreading the jaws of an animal, the animal having a lower jaw having lower front teeth, an upper jaw having upper front teeth, the lower jaw having a chin, the jaws of the animal having a right and left side, the animal having a head having a back portion, comprising the steps of:

providing a speculum having first arm having a first end and an opposite second end, a first jaw plate pivotally connected to said first end of said first arm, a second arm oriented substantially parallel to said first arm, said second arm having a first end and an opposite second end, a second jaw plate pivotally connected to said first end of said second arm, a threaded rod, said threaded rod having an end portion rotatably connected to said first arm, and a second end opposite to said end portion, said threaded rod substantially perpendicular to said first arm, said second arm having a threaded aperture which threadably receives said threaded rod, a retaining means for keeping said first and second arms rotationally aligned around said threaded rod, said first jaw plate contoured to receive the lower front teeth, and said second jaw plate contoured to receive the upper front teeth;

providing a tension-producing means having a length, a first end and an opposite second, said first end of said tension-producing means connected to said first and second jaw plates;

rotating said threaded rod until said first arm and said second arm are separated by a predetermined distance;

placing said second end of said tension-producing means around the back portion;

adjusting said length of said tension producing means so that said speculum resides slightly behind and below the animal's chin;

stretching said tension-producing means;

inserting said speculum between the jaws so that said first jaw plate receives the lower front teeth, and said second jaw plate receives the upper front teeth;

rotating said threaded rod so that said predetermined distance is increased and the jaws are thereby urged apart; and, selectively pivoting said first and second arms to either the right or left side.

11. The method according to claim 10, further including the steps of:

providing a socket connected to said second end of said threaded rod;

providing a powered rotational tool;

inserting the powered rotational tool into said socket;

said step of rotating further including activating the powered rotational tool to effect said rotation.

12. The method according to claim 10, further including the step of:

pulling said speculum forward to remove it from the animal's teeth and jaws.

13. A speculum for the jaws of an animal, the jaws of the animal having a right and left side, comprising:

a first arm having a first end and an opposite second end, a first jaw plate pivotally connected to said first end of said first arm;

a second arm oriented substantially parallel to said first arm, said second arm having a first end and an opposite second end, a second jaw plate pivotally connected to said first end of said second arm;

a threaded rod, said threaded rod having an end portion rotatably connected to said first arm, said threaded rod substantially perpendicular to said first arm, said threaded rod having a second end opposite to said end portion;

said second arm having a threaded aperture which threadably receives said threaded rod, said second arm located a distance from said first arm;

so that by rotating said threaded rod, said distance may be selectively adjusted;

a retaining means for keeping said first and second arms rotationally aligned around said threaded rod; and, said first and second arms selectively pivotable to either the right or left side.

* * * * *